(12) United States Patent
Jaracz et al.

(10) Patent No.: US 9,625,449 B2
(45) Date of Patent: Apr. 18, 2017

(54) DETERMINING THE BIOAVAILABILITY OF ZINC (II) IONS

(71) Applicant: Colgate-Palmolive Company, Piscataway, NJ (US)

(72) Inventors: Stanislav Jaracz, Somerset, NJ (US); Harsh M. Trivedi, Hillsborough, NJ (US); Lyndsay Schaeffer-Korbylo, Flemington, NJ (US); Lynette Zaidel, Cranbury, NJ (US)

(73) Assignee: Colgate-Palmolive Company, New York, NY (US)

( * ) Notice: Subject to any disclaimer, the term of this patent is extended or adjusted under 35 U.S.C. 154(b) by 98 days.

(21) Appl. No.: 14/580,485

(22) Filed: Dec. 23, 2014

(65) Prior Publication Data
US 2016/0178617 A1 Jun. 23, 2016

(51) Int. Cl.
*G01N 21/78* (2006.01)
*G01N 33/84* (2006.01)
*G01N 33/50* (2006.01)

(52) U.S. Cl.
CPC ......... *G01N 33/5082* (2013.01); *G01N 21/78* (2013.01); *G01N 33/84* (2013.01)

(58) Field of Classification Search
None
See application file for complete search history.

(56) References Cited

U.S. PATENT DOCUMENTS

| | | | |
|---|---|---|---|
| 4,289,754 A | 9/1981 | Dhabhar et al. | |
| 4,992,259 A | 2/1991 | Schiraldi et al. | |
| 5,330,748 A | 7/1994 | Winston et al. | |
| 6,159,459 A | 12/2000 | Hunter et al. | |
| 2004/0001897 A1 | 1/2004 | Amano et al. | |
| 2014/0024010 A1 | 1/2014 | Akashi et al. | |

FOREIGN PATENT DOCUMENTS

| | | |
|---|---|---|
| WO | WO0172347 | 4/2001 |
| WO | WO03/088957 | 10/2003 |
| WO | WO2007/013937 | 2/2007 |
| WO | WO2008/041055 | 4/2008 |
| WO | WO2011028878 | 3/2011 |
| WO | WO2011108300 | 9/2011 |
| WO | WO2011/016984 | 10/2011 |

OTHER PUBLICATIONS

Yang et al., Retention of o-cymen-5-ol and zinc on reconstructed human gigival tissue from a toothpaste formulation, International Dental Journal 2011; 61 (Suppl. 3): 41-45.*
Mohammed et al., Physical chemical effects on zinc on in vitro enamel demineralization, Journal of Dentistry 42 (2014) 1096-1104.*
Anonymous, "Fluorescent Indicators for Zn2+ and other metal ions", The Molecular Probes Handbook, Life Technologies Inc, http://www.lifetechnologies.com/uk/en/home/references/molecular-probes-the-handbook/indicators-for-ca2-mg2-zn2-and-other-metal-ions/fluorescent-indicators-for-zn2-and-other-metal-ions.html accessed Nov. 13, 2014.
Anonymous, Standard Electrode Potential (data page), http://en.wikipedia.org/wiki/Standard_electrode_potential_(data_page), accessed Nov. 13, 2014.
Areco et al., 2007, "Zinc Biosorption by Seaweed Illustrated by the Zincon Colorimetric Method and the Langmuir Isotherm", Journal of Chemical Education, vol. 84, No. 3, pp. 302-305.
Brading et al., 2009, "Gum health benefits of a silica based fluoride toothpaste containing zinc citrate, potassium citrate, hydroxyapatite and vitamin E acetate", International Dental Journal, 59, pp. 332-337.
Brophy et al., 2012, "Calcium ion gradients modulate the zinc affinity and antibacterial activity of human calprotectin", J Am Chem Soc, 134, 43, pp. 18089-18100.
Chen et al., 2001, "Catalytic selenols couple the redox cycles of metallothionein and glutathione", European Journal of Biochemistry, 268, 3346-3353.
Clever et al., 1992, "The Solubility of Some Sparingly Soluble Salts of Zinc and Cadmium in Water and in Aqueous Electrolyte Solutions", J Phys Chem Ref Data, 21, 5, pp. 941-966.
Ejnik et al., 2010, "Mechanism of Cadmium Ion Substitution in Mammalian Zinc Metallothionein and Metallothionein Alpha Domain; Kinetic and Structural Studies", Inorg. Chem., 49, pp. 6525-6534.
Gulson et al., 2010, "Small amounts of zinc from zinc oxide particles in sunscreens applied outdoors are absorbed through human skin", Toxicological Sciences, 118, 1, pp. 140-149.
Harrap et al., 1984, "Human oral retention of zinc from mouthwashes containing zinc salts and its relevance to dental plaque control", Archs Oral Biol., 29, 2, pp. 87-91.
He et al., 2002, "Inhibitory effect of ZnCl2 on glycolysis in human oral microbes", Archs Oral Biol, 47, 2, pp. 117-129.
Klemm, 2011, "Microelectrochemical characterization of Zn, ZnO and Zn—Mg alloys with online dissolution monitoring", Ruhr University Bochum, Germany.
Mabrouk et al., 1992, "Direct electrochemical synthesis of cobalt, nickel, copper, zinc, cadmium, tin and lead complexes", Trans Met Chem, 17, pp. 1-4.
Mitra et al., 1960, "The reaction between polyvalent metal cations and alkali metal pyrophosphates" Proc Nat Inst Sci India, 26A, pp. 151-161.

(Continued)

*Primary Examiner* — Suzanne M Noakes
*Assistant Examiner* — Stephen Chong

(57) ABSTRACT

An in vitro method for determining the bioavailability of zinc (II) ions from an oral care composition comprises: providing a sample comprising, the oral care composition; contacting the sample with a biorelevant substrate, separating the biorelevant substrate from the sample, contacting the biorelevant substrate with an indicator under conditions selected such that the indicator is capable of reacting with zinc (II) ions, and determining a light absorbance of the indicator. The indicator is zincon or a salt thereof. The method is useful for estimating the ability of an oral care composition to deliver therapeutically-active zinc (II) ions to the oral cavity. Also provided is the use of zincon and a biorelevant substrate in vitro to determine the bioavailability of zinc (II) ions from an oral care composition comprising, a zinc source.

16 Claims, 1 Drawing Sheet

(56) References Cited

OTHER PUBLICATIONS

Motozova et al., 1976, Zn2P2O7—K4P2O7—H2O System at 25°,. J Inorg Chem, 12(6):878.

Nevitt et al., 1958, "Topical applications of sodium fluoride and stannous fluoride", Public Health Rep, vol. 73, No. 9, pp. 847-850.

Ozedimir et al., 1998, "The Determination of Salivary Zinc Level Following Delivery from Zinc Containing Toothpaste", Tr. J. of Medical Sciences, 28, pp. 281-283.

Rakhmatullina et al., 2013, "Inhibition of enamel erosion by stannous and fluoride containing rinsing solutions", Schweiz Monatsschr Zahnmed, vol. 123, pp. 192-197.

Richter et al., 2002, "Solid phase spectrophotometric determination of copper in water by using immobilized zincon in a sephadex A25 resin", Anal. Lett. 35, pp. 635-646.

Skog et al., 1964, "A comparative investigation of the percutaneous absorption of metal compounds in the guinea pig by means of radioactive isotopes: 51Cr, 58Co, 65Zn, 110mAg, 115mCd, 203Hg", J Invest Dermatol, 43, 3, pp. 187-192.

Thompson, 1989. "Chapter 22: Zinc Links: Coordination Chemistry and Nutritional Deficiency" in "Chemtrek Small Scale Experiments for General Chemistry", Prentice Hall, NJ, USA.

Wilcox, 2009, "The black and white of immersion tin: keeping an eye on cupric ions can eliminate black tin", Printed Circuit Design & Fab, Jul. 1, 2009.

Yoe et al., 1952, "A new colorimetric reagent for zinc", Anal, Chim, Acta, vol. 6, pp. 526-527.

Zhang, et al., 2009, "Effect of resveratrol and zinc on intracellular zinc status in normal human prostate epithelial cells", Am J Physiol Cell Physiol, 297, C632-C644.

\* cited by examiner

DETERMINING THE BIOAVAILABILITY OF ZINC (II) IONS

TECHNICAL FIELD

The present invention generally relates to an in vitro method for determining the bioavailability of zinc (II) ions from an oral care composition. Also provided is the use of an indicator and a biorelevant substrate to determine the bioavailability of zinc (II) ions from an oral care composition.

BACKGROUND

Oral care compositions, such as toothpastes, may comprise zinc complexes as active ingredients. Zinc (II) ions are useful in the treatment of various diseases and disorders of the oral cavity. For example, zinc (II) has been used in the treatment of halitosis and as an antiplaque agent.

It has been reported previously that only free zinc (II) ions display these useful effects (U.S. Pat. No. 4,992,259). Oral care compositions are generally complex mixtures of multiple ingredients. Certain ingredients may interact with zinc and limit its availability. In most cases, the ability of a composition to release zinc (II) is not readily predictable and must be determined empirically.

Various methods for measuring the amount of zinc delivered by a composition have been proposed.

Atomic absorption spectroscopy (AAS) is useful for the quantitative determination of various elements, and has been used to measure the amount of zinc present in saliva following toothbrushing (Ozedimir et al, 1998. "The Determination of Salivary Zinc Level Following Delivery from Zinc Containing. Toothpaste", Tr. J. of Medical Sciences, 28. pp 281-283).

The use of a zinc composition enriched with a stable zinc isotope ($^{68}$Zn) with detection by multi-collector inductively coupled plasma mass spectrometry (MC-ICP-MS) has been applied to the analysis of the absorption of zinc oxide particles from sunscreens by human skin (Gulson et al. 2010. "Small amounts of zinc from zinc oxide particles in sunscreens applied outdoors are absorbed through human skin" Toxicological Sciences, 118, 1, pp 140-149). The unstable zinc isotope $^{65}$Zn has also been used to investigate the percutaneous absorbtion of zinc in the guinea pig (Skog and Wahlberg, 1964. "A comparative investigation of the percutaneous absorption of metal compounds in the guinea pig by means of radioactive isotopes: $^{51}$Cr, $^{58}$Co, $^{65}$Zn, $^{110m}$Ag, $^{115m}$Cd, $^{203}$Hg", J Invest Dermatol, 43, 3, pp 187-192).

Although these methods allow the quantitation of absorbed zinc, they do not discriminate between therapeutically-active zinc (II) ions and inactive bound zinc. Furthermore, relatively complex apparatus is required. There remains a need in the art for a rapid and simple method for estimating the therapeutically-active zinc delivered by an oral care composition.

BRIEF SUMMARY

In one aspect, the present invention provides an in vitro method for determining the bioavailability of zinc (II) ions from an oral care composition comprising a zinc source, which method comprises: (i) providing a sample comprising the oral care composition; (ii) contacting the sample with a biorelevant substrate; (iii) separating the biorelevant substrate from the sample; (iv) contacting the biorelevant substrate with an indicator under conditions selected such that the indicator is capable of reacting with zinc (II) ions; and (v) determining a light absorbance of the indicator; wherein the indicator is zincon or a salt thereof. It has surprisingly been found that the results obtained using the method show good correlation with those of hi vim clinical studies. The method allows the rapid, straightforward estimation of in vivo zinc delivery.

The biorelevant substrate may be a soft tissue or a mimetic thereof. It has been found that zincon is particularly useful for determining the uptake of zinc by soft tissues. The soft tissue is preferably dermal tissue or a tissue from the oral cavity. The soft tissue mimetic is preferably a dermal tissue mimetic or a mimetic of a tissue from the oral cavity. Particularly preferably, the biorelevant substrate is a synthetic skin. Unlike naturally-derived tissue samples, synthetic skin is not susceptible to microbial decomposition and requires no special handling.

The oral care composition may be a toothpaste. In this arrangement, the sample is advantageously a slurry comprising the toothpaste and a solvent. The ratio of the toothpaste to the solvent by weight may be in the range 1:1 to 1:4. These conditions approximate the manner in which toothpastes are used by consumers and therefore allow a more reliable prediction of in vivo bioavailability of the zinc.

The sample may include natural or artificial saliva. This allows the conditions in the oral cavity to be approximated more closely.

The indicator may be provided in an aqueous solution having a pH in the range of 7 to 9.5. The reaction between zincon and zinc (II) proceeds most easily in this pH range. Preferably, the aqueous solution has a pH in the range of 7 to 8. This range approximates the conditions found in the oral cavity.

The aqueous solution may further comprise a thickener. Thickeners are useful for increasing the viscosity of the solution. Increased viscosity improves the contact with the biorelevant substrate and the zincon during step (iv).

Step (ii) may comprise incubating the biorelevant substrate with the sample for a total duration in the range 10 to 60 minutes, optionally 10 to 20 minutes. It has been found that this duration of contact enables a strong signal to be obtained.

Step (v) may comprise: (a) capturing a digital image of the biorelevant substrate; and (b) analysing the image in software. Image analysis allows a quantitative estimate of the amount of zinc delivered to be obtained.

In another aspect, the present invention provides the use of zincon and a biorelevant substrate in vitro to determine the bioavailability of zinc (II) ions from an oral care composition comprising a zinc source. Zincon selectively binds zinc (II) ions in preference to the $Ca^{2+}$ and $Mg^{2+}$ commonly found in biorelevant substrates. Zincon is moreover selective for free zinc (II) ions. These properties render it particularly useful for the analysis of oral care compositions.

The biorelevant substrate may be a soft tissue or a mimetic thereof. It has been found that zincon is particularly useful for determining the uptake of zinc by soft tissues. The soft tissue is preferably dermal tissue or a tissue from the oral cavity. The soft tissue mimetic is preferably a dermal tissue mimetic or a mimetic of a tissue from the oral cavity. Particularly preferably, the biorelevant substrate is a synthetic skin. Unlike naturally-derived tissue samples, synthetic skin may be stored in a dried form and is therefore not susceptible to microbial decomposition.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, in which.

DETAILED DESCRIPTION

Figure 1:
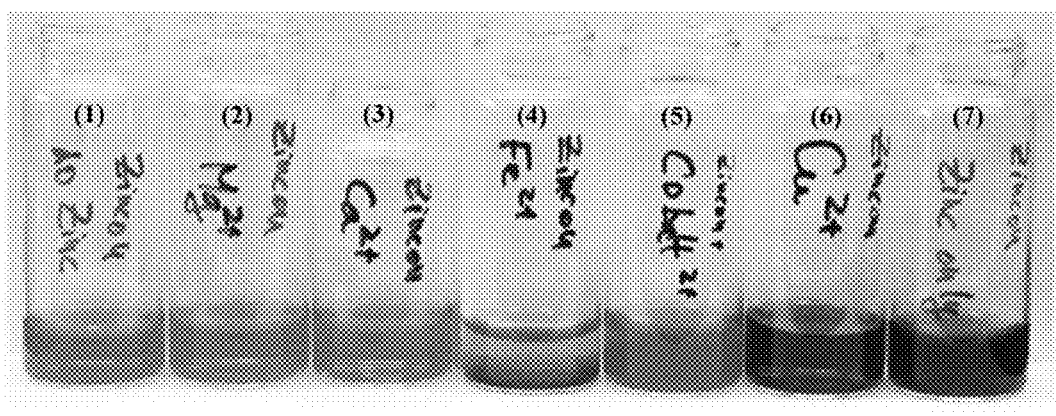
FIG. 1 is a photograph of vials containing solutions 1 to 6, as discussed in Reference Example 2.

The following description of the preferred embodiments is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As used herein, the term "zincon" refers to o-[α-(2-hydroxy-5-sulfophenyl azo)-benzylidene hydrazino]benzoic acid, which has CAS number 56484-13-0. The structure of the sodium salt of zincon is as follows:

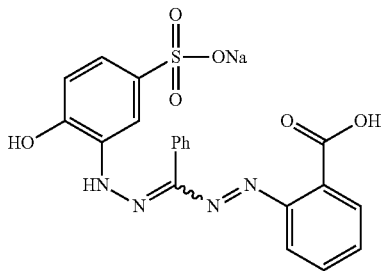

In the context of the present invention, a biorelevant substrate is a material which is an in vitro model of a biological tissue. The biorelevant substrate is advantageously an in vitro model of a soft and hard tissue found in the oral cavity of a human.

Generally, the tissue to be modeled will be a soft and hard tissue found in the oral cavity. The biorelevant substrate may therefore be a soft and hard tissue from the oral cavity. Examples of such tissues include gum, tongue, buccal tissue and teeth. It has also been found that dermal tissue is a useful model of the soft tissues of the oral cavity and calcium-based minerals is a useful model for the hard tissue. Illustrative examples of suitable biorelevant substrates for modeling soft tissue include tissue samples, cell cultures, and synthetic skin models. Examples of suitable biorelevant substrates for modeling hard tissue include hydroxyapatite disc and sea shells. Example of HAP disc is Calcium Deficient HA Disc from a vendor Himed Inc. Old Bethpage, N.Y., US.

The tissue samples useful herein include samples of tongue or skin from a mammal, such as a pig. The preferred tissue sample is pig tongue. Useful cell cultures include cultures of human gum or buccal cells.

Preferably, the biorelevant substrate is a synthetic skin model. A particularly preferred synthetic skin model is marketed by Innovative Measurement Solutions Inc, Portland, US under the trade name VITRO-SKIN.

Other illustrative examples of synthetic skin models include those described in US20140024010, WO2011108300, WO2001072347, US20040001897, and WO2011028878.

Zincon is a coloured dye which appears to be red in aqueous solution. Contacting zincon with zinc (II) ions results in the formation of a blue complex. The use of zincon as an indicator for zinc in solution has been described previously (Yoe and Rush, 1952. "A new colorimetric reagent for zinc", Anal. Chim. Acta, vol. 6, pp 526-527). The use of zincon in solution to detect unbound zinc (II) in the presence of ligands has also been proposed (WO03/088957).

It has now surprisingly been found that zincon may be used to determine the extent to which zinc (II) ions are taken up by biorelevant substrates. Previous approaches to measuring the uptake of zinc by substrates have generally relied, upon the use of atomic absorption spectroscopy (AAS). These existing methods require a considerable amount of sample preparation (for example, the digestion of tissue samples) and the use of specialized apparatus. The methods provided herein allow for the rapid estimation of the relative amount of zinc taken up by biorelevant substrates from oral care compositions. The methods are useful for the comparison and ranking of oral care compositions based on their ability to deliver zinc. The rankings thus obtained show good correlation with the results obtained, using conventional AES techniques.

It has previously been reported that only free zinc (III) ions are therapeutically-useful in oral care applications (see e.g. U.S. Pat. No. 4,992,259). In comparison to other indicators for the detection of zinc, such as Eriochrome Black T (sodium 1-[1-hydroxynapthylazo]-6-nitro-2-napthol-4-sulfonate) and 4-(2-pyridylazo) resorcinol (PAR) zincon binds zinc (II) weakly. This means that in the presence of chelating agents or other ligands which restrict the bioavailability of zinc (II) ions, no reaction between zincon and zinc takes place. As will be discussed in more detail in the Examples, it has surprisingly been found that ligands which prevent the reaction between zincon and zinc also limit the antimicrobial activity of zinc.

Biorelevant substrates, and in particular samples of natural tissues, may contain various metal ions. Important metal ions encountered in biological tissues include magnesium (II) and calcium (II). Many dyes which react with zinc (II) will also react with magnesium (II) and/or calcium (II), and would lead to false positives if used in the present methods. Although the electrochemical synthesis of various metal-zincon complexes has been reported (Mabrouk et al, 1992, "Direct electrochemical synthesis of cobalt, nickel, copper, zinc, cadmium, tin and lead complexes", Trans Met Chem, 17, pp 1-4), zincon does not appear to undergo a colour change in the presence of calcium or magnesium (see Examples). This contributes to zincon's utility for the detection of zinc in biorelevant substrates.

Thus, zincon's selectivity for unbound zinc (II) ions enables the detection of bioavailable zinc ions in biorelevant substrates.

Provided herein is an in vitro method for determining the bit availability of zinc (II) ions from an oral care composition comprising a zinc source.

The nature of the oral care composition is not particularly limited. One of skill in the art will be familiar with the formulation of oral care compositions. Oral care compositions generally comprise an oral care active and an orally-acceptable carrier. Illustrative examples of oral care compositions include toothpastes, tooth gels, tooth powders, and mouth rinses. Examples of ingredients which may be present in oral care compositions include abrasives, polymers, enzymes, humectants, thickeners, viscosity modifiers, antimicrobial agents, chelating agents, pH adjusting agents, preservatives, flavorings, sweeteners, whitening agents, colorants, and herbal extracts.

Oral care compositions useful herein are generally substantially free of copper (II) ions. Zincon forms a blue complex with copper (II). An oral care composition may be considered substantially free of copper (II) ions if, for example, it contains less than 5 ppm copper (II) by weight.

Since the zinc (II) is detected using a change in the light absorbance of the zincon, for certain applications the oral care composition may advantageously be substantially free of soluble colourants. An oral care composition may be considered substantially free of soluble colourants if a mixture consisting of 4 parts water to 1 part oral care composition by weight has a UV absorbance in the visible spectrum (390 to 700 nm) of 0.05 units or less at a path length of 1 cm, following filtration or centrifugation to remove any insoluble components. Generally, the colourants used in oral care compositions will not stain biorelevant substrates and their presence is therefore readily tolerated.

The oral care composition includes a zinc source. The term zinc source refers generally to zinc, salts, zinc complexes, and other compounds containing zinc. The nature of the zinc source is not particularly limited. Illustrative examples of zinc sources include zinc acetate, zinc acetylacetonate, zinc ammonium sulfite, zinc benzoate, zinc bromide, zinc borate, zinc butylphthalate, zinc butylxanthate, zinc caprylate, zinc carbonate, zinc chloroanilate, zinc citrate, zinc cyclohexanebutyrate, zinc chloride, zinc gallate, zinc fluoride, zinc alpha-glucoheptonate, zinc gluconate, zinc glycerophosphate, zinc hydroxide, zinc 12-hydroxystearate, zinc iodide, zinc acrylate, zinc oxide, zinc propionate, zinc isovalerate, zinc D-lactate, zinc DL-lactate, zinc laurate, zinc hexafluorosilicate, zinc methacrylate, zinc molybdate, zinc naphthenate, zinc octoate, zinc oleate, zinc orthophosphate, zinc phenolsulfonate, zinc pyridine-2-thiol-1-oxide, zinc pyrophosphate, zinc resinate, zinc salicylate, zinc sulfate, zinc nitrate, zinc selenide, zinc stearate, zinc sulfanilate, zinc tartrate, zinc tellurate, zinc tungstate, zinc valerate, zinc vanadate, and zinc tribromosalicylanilide.

The methods described herein include the step of providing a sample comprising the oral care composition.

The form of the sample is not particularly limited and may be selected as appropriate depending on the nature of the oral care composition. If the oral care composition is in the form of a mouth rinse, the sample may consist of the oral care composition. If the oral care composition is in the form of a toothpaste, a tooth gel, or a tooth powder, then the sample is advantageously in the form of a slurry comprising the oral care composition and a solvent.

In the arrangements where the sample is a slurry, the solvent is typically water. This is representative of the conditions under which most toothpastes, tooth gels and tooth powders are used by consumers, thereby allowing a more reliable estimate of the ability of the composition to deliver zinc (II) ions to be obtained. The ratio of oral care composition to solvent present in the slurry is not particularly limited, but is typically in the range of 1:1 to 1:20 by weight. Preferably, the ratio of oral care composition to solvent is in the range 1:1 to 1:4.

The sample may include natural or artificial saliva. The preferred natural saliva is human saliva. The natural saliva may be pre-treated, for example clarified or sterilised, before use. One of skill in the art will be familiar with the formulation of artificial salivas. Artificial salivas are also referred to in the art as oral moisturisers, and include those artificial salivas marketed for the relief of disorders such as xerostomia. Typical ingredients included in artificial salivas include rheology modifiers, salts, and proteins. Examples of artificial salivas are disclosed in U.S. Pat. No. 6,159,459.

The methods provided herein include the step of contacting the sample with the biorelevant substrate. The biorelevant substrate and the sample may be contacted in any desired manner. The sample is typically in the form of a liquid or suspension, and this step therefore most conveniently comprises submerging the biorelevant substrate in the sample.

The amount of zinc (II) delivered to the substrate by the sample will vary depending on the duration of contact between the sample and the substrate, as well as on their natures. Longer contact durations result in the delivery of more zinc (II) and hence a stronger signal. For the compositions investigated in the Examples, it was found that the optimum duration of contact was in the range 10 minutes to 60 minutes, preferably about 15 minutes. This duration of contact allowed, a readily detectable amount of zinc (II) to be delivered.

The methods include the step of separating the biorelevant substrate from the sample. This step may include rinsing the substrate with a solvent, e.g. to remove any loose particulate matter deposited from a slurry.

The methods include the step of contacting the biorelevant substrate with an indicator under conditions selected such that the indicator is capable of reacting with zinc (II) ions. The indicator is zincon or a salt thereof.

Zincon is an ionizable compound. Zincon may therefore be provided in the form of a salt. The counterion present in the salt is selected such that the counterion does not interfere with the detection of zinc ions. Suitable salts may be identified for example by contacting, the salt with a solution known to contain zinc (II) ions. If a blue complex is formed, then the counterion is suitable. A preferred salt is zincon monosodium, which is commercially available.

The zincon is most preferably provided in an indicator composition, suitably air aqueous solution. The solution may comprise the zincon, a solvent and optionally one or more additives. Zincon is poorly soluble in many organic, solvents. The solvent therefore preferably comprises water. Examples of suitable solvents include water and aqueous cosolvent mixtures, for example mixtures comprising water and an alcohol or a ketone. Useful alcohols include C1 to C4 linear or branched alkyl alcohols, such as methanol, ethanol, and isopropanol. Useful ketones include acetone and the like.

In the arrangements where the solvent comprises water, the pH of the solution may be in the range of 7 to 10 and preferably 8.5 to 9.5. Zincon has acidic functional groups which become ionized at alkaline pH. Providing a solution which is mildly alkaline therefore assists in dissolving the zincon and facilitates the reaction of zincon with positively-charged metal ions.

The solution may comprise a buffer for maintaining, the pH within the desired range. One of skill in the art will be familiar with aqueous buffer solutions. The buffer preferably does not comprise a chelating agent. Zinc ions are bound by zincon weakly, and the presence of chelating agents in the buffer may therefore interfere with their detection. Examples of useful buffers include ammonium buffer, suitably at a pH in the range of 8.5 to 9.5; TRIS, suitably at a pH in the range of 7 to 9; and HEPES, suitably at a pH in the range of 7 to 75.

The amount of zincon present in the indicator composition may be selected as appropriate. For example, zincon may be present in the indicator composition in an amount in the range 0.01% to 1% optionally 0.1% to 1% by weight of the indicator composition. Preferably, the amount of zincon present in the solution is in the range 0.2% to 0.4% by weight. This range was found to provide particularly good data when used to analyse typical oral care compositions containing up to 1% zinc source by weight. Higher concentrations of zincon, for example in the range 0.5-1% may be desirable for assays involving larger dilutions.

Various additives may be included in the indicator composition. Examples of such additives include preservatives for extending shelf life and thickeners. The preferred additives are thickeners. By increasing the viscosity of the indicator composition, thickeners ensure that the indicator composition remains in contact with the biorelevant substrate. A preferred thickener is xanthan gum. The thickener may be present in the indicator composition in an amount in the range of 0.1% to 0.3% by weight.

The indicator may be contacted with the substrate using any appropriate method known in the art. When the indicator is supplied in the form of a solution, the solution may be applied to the substrate by dipping, spraying, or application using a pipette or dropper. In the arrangements where image analysis is to be carried out, the use of a pipette is particularly preferred because this allows fine control over the amount of zincon added to the substrate, improving, the reliability of the subsequent analysis.

The method includes the step of determining, as light absorbance of the indicator.

Zincon undergoes a colour change from red to blue in the presence of zinc (II). Therefore, this step may involve the visual observation of the colour of the zincon after it has been applied to the substrate. The intensity of the blue colour correlates with the amount of zinc (II) delivered to the substrate. The side-by-side comparison of a series of samples may therefore be undertaken to allow the ranking of oral care compositions. Standard compositions having a known ability to deliver zinc (II) may be used for the purposes of calibration.

This step may include capturing a digital image of the biorelevant substrate and analysing the image in software.

The image is most conveniently captured using a digital camera. The use of a conventional camera in combination with a scanner is also contemplated herein.

The digital camera suitably has a resolution of at least 3 megapixels. The digital camera is preferably configured such that the white balance of the images captured by the camera may be calibrated. Digital cameras with these capabilities are commercially available.

White balance may be calibrated using a commercially available calibration sheet, for example a Munsell Color Control Standard, in accordance with the manufacturer's instructions. Calibration of the white balance of the camera improves the reproducibility of the results obtained.

The image is suitably captured in daylight or under white fluorescent lighting, without the use of a flash. Fluorescent lighting is less variable than ambient daylight and is therefore particularly preferred. Images are suitably captured against a white background. The exposure bias of the camera may be adjusted to increase the whiteness of the image.

The camera may be provided with support means, for example a frame or tripod, for holding the camera a fixed distance from the background. Fixing the camera in position improves the reliability of image capture.

The image analysis typically involves processing the image using a software package capable of deriving a measure of the amount of blue colour present in the image. Preferably, the colour mode of the image is convened to Lab before measuring the b-value (blue hue). A suitable software package is Adobe Photoshop. The b-value has been found to correlate with the amount of zinc (II) taken up by the substrate. The image analysis typically involves the generation of a colour histogram. The precise threshold chosen for identifying a pixel as blue is not critical, provided that a consistent threshold is used when comparing samples. Optimisation of the threshold level based on the colour produced by zincon on the chosen substrate may improve the accuracy of the measurement.

An illustrative method for image capture and analysis is described in Example 1. The image capture may be substantially as described in Example 1. The image analysis may be substantially as described in Example 1. The image capture and analysis methods of Example 1 may be applied to samples and substrates different to those illustrated in the Example.

Also provided is the use of zincon and a biorelevant substrate in vitro to determine the bioavailability of zinc (II) ions from an oral care composition comprising a zinc source. The use may be in a method as described above. It will be appreciated that the technical considerations set out above with reference to the method are equally applicable to the use.

The zincon may be in the form of an aqueous solution. Preferred features of the aqueous solution are described above with reference to the methods of the present disclosure. The biorelevant substrate and/or the oral care composition may be as described above with reference to the methods.

EXAMPLES

The present invention will now be explained by reference to the following non-limiting examples.

Reference Example 1

Use of Zincon to Predict Antibacterial Activity

To illustrate that zincon is useful for the detection of bioavailable zinc (II) ions, the reaction of zincon with $Zn^{2+}$ in the presence of various ligands was investigated. It was found in subsequent cell viability assays that ligands which prevented or inhibited the reaction between $Zn^{2+}$ and zincon showed weaker antibacterial activity than those which did not.

An indicator was prepared by dissolving zincon sodium salt in a 0.2 M ammonia buffer. The pH of the buffer was 9.25. The amount of zincon sodium salt present in the indicator was 0.3% by weight. A series of test solutions was then prepared. Each test solution included 2 to 3 mL, of deionised water, 1 mL of ammonia buffer, and 40 μL of the indicator solution. The remaining components of the solution are set out in Table 1:

TABLE 1 solutions investigated. Ligands A to C are each candidate materials for inclusion in an oral care composition.

| | Additive |
|---|---|
| Solution 1 | None |
| Solution 2 | 100 μL of 0.25M Zn(NO$_3$)$_2$, 300 μL of 0.25M Ligand A |
| Solution 3 | 100 μL of 0.25M Zn(NO$_3$)$_2$, 300 μL of 0.25M Ligand B |
| Solution 4 | 100 μL of 0.25M Zn(NO$_3$)$_2$, 300 μL of 0.25M Ligand C |
| Solution 5 | 100 μL of 0.25M Zn(NO$_3$)$_2$ |

In the absence of zinc (II) ions, zincon is red in colour. The complexation of zinc (II) ions by zincon results in a colour change from red to blue. A blue colour is observed even in the presence of ligand C, suggesting that this ligand does not bind zinc, strongly. No colour change was observed in the presence of ligand A. This suggests that ligand A binds zinc (II) strongly, rendering it unavailable for reaction with zincon. An orange-brown colour was observed in the presence of ligand B, suggesting that some zinc (II) was available for reaction with zincon.

In order to illustrate that the results obtained using zincon are predictive of therapeutic activity, a series of cell viability assays were performed. Cell cultures containing a set of bacterial strains were contacted with zinc and various ligands. The bacterial strains were selected so as to be representative of the bacteria found in the oral cavity. Cell viability was then assessed using, resazurin dye (7-hydroxy-3H-phenoxazin-3-one 10-oxide) in accordance with a standard procedure.

Results of the cell viability assays are shown in Table 2.

TABLE 2 viability of cells contacted with zinc and various ligand salts

| Ligand salt | Cell viability/% |
|---|---|
| Ligand A | 34.51 |
| Ligand B | 28.15 |
| Ligand C | 12.97 |

The data illustrate that a stung antimicrobial effect was observed in the presence of ligand C. A moderate antimicrobial effect was observed in the presence of ligand B. The weakest antimicrobial effect was observed in the presence of ligand A. This is in line with the results obtained using zincon.

Accordingly, the use of zincon allows for the rapid assessment of the likely antimicrobial activity of a zinc-containing composition.

Reference Example 2

Reactions of Zincon with Various Metal Ions

Certain dyes used to detect zinc ions also react with other metal ions. For example, Eriochrome Black T reacts with $Mg^{2+}$ and $Ca^{2+}$ ions, which are commonly encountered in biological tissues. Sources of calcium ions are frequently included in oral care compositions. Hence, there would be a risk of false positives if this dye were to be used as an indicator for zinc released from oral care compositions. In order to illustrate that zincon displays good selectivity for zinc, solutions comprising, zincon and various metal ions were prepared.

The solutions investigated are set out in Table 3:

TABLE 3 metal ions investigated

| Solution | Metal ion |
|---|---|
| 1 | None |
| 2 | $Mg^{2+}$ |
| 3 | $Ca^{2+}$ |
| 4 | $Fe^{2+}$ |
| 5 | $Co^{2+}$ |
| 6 | $Cu^{2+}$ |
| 7 | $Zn^{2+}$ |

A photograph of the solutions is shown in FIG. 1. Vials containing solutions 1 to 7 are shown from left to right.

Zincon did not undergo a colour change in the presence of $Mg^{2+}$ or $Ca^{2+}$, suggesting that no complex is formed between zincon and these ions. It is therefore believed that the presence of $Mg^{2+}$ and $Ca^{2+}$ would not prevent the successful detection of $Zn^{2+}$. This property renders zincon particularly useful for the analysis of oral care compositions and biorelevant substrates.

Colour changes were observed in the presence of $Fe^{2+}$, $Co^{2+}$, and $Cu^{2+}$. $Fe^{2+}$ and $Co^{2+}$ produced colour changes which are distinguishable from the deep blue complex formed between zincon and $Zn^{2+}$; $Fe^{2+}$ formed a green solution and $Co^{2+}$ formed a sky blue solution. The colour produced by $Cu^{2+}$ is difficult to distinguish from that of $Zn^{2+}$.

Only trace amounts of $Co^{2+}$ and $Cu^{2+}$ are present in biological tissues and tissue mimetics. Free $Fe^{2+}$ is not commonly encountered in biological systems or tissue mimetics. Moreover, none of $Co^{2+}$, $Cu^{2+}$ and $Fe^{2+}$ are generally included in oral care compositions.

Accordingly, zincon shows selectivity for zinc over the $Ca^{2+}$ and $Mg^{2+}$ ions found in biorelevant substrates or oral care compositions. Although zincon is capable of forming complexes with $Co^{2+}$, $Cu^{2+}$ and $Fe^{2+}$, these ions are not expected to interfere with the detection of zinc on the substrates used in the present invention.

Reference Example 3

Effect of pH on the Detection of Zinc (II) Using Zincon

It has been reported in the literature that the working pH range for zincon is pH 8.5 to 9.5 (Yoe and Rush, 1952. "A new colorimetric reagent for zinc", Analytica Chimica Acta, vol. 6, pp 526 to 527). Experiments were conducted to illustrate that zincon may be used at pHs outside this range.

TABLE 4 absorbance of zincon as function of pH

| pH | Absorbance of blank at 610 nm | Absorbance of sample at 610 nm |
|---|---|---|
| 7.0 | 0.040 | 0.233 |
| 7.5 | 0.036 | 0.232 |
| 8.0 | 0.035 | 0.245 |

TABLE 4-continued absorbance of zincon as function of pH

| pH | Absorbance of blank at 610 nm | Absorbance of sample at 610 nm |
|---|---|---|
| 8.5 | 0.036 | 0.251 |
| 9.5 | 0.035 | 0.252 |

As shown in the table above, zinc was detected successfully at all of the pHs investigated.

Further experiments were conducted using oral care compositions.

Four toothpaste compositions (compositions W, X, Y and Z) each containing at least one zinc source were prepared. The compositions were dispersed in deionised water to form slurries. The ratio of the toothpaste composition to deionised water, by weight, was 1:2. The slurries were centrifuged for 10 minutes at 10,000 rpm. Samples of the resulting supernatant (100 µL) were each added to 2 to 3 mL, of HEPES buffer (0.1 M, pH 7) and 20 µL of a 0.3% solution of zincon sodium. The resulting solutions were stirred briefly. The tests were repeated using an ammonia buffer at pH 9.

Figure 2:
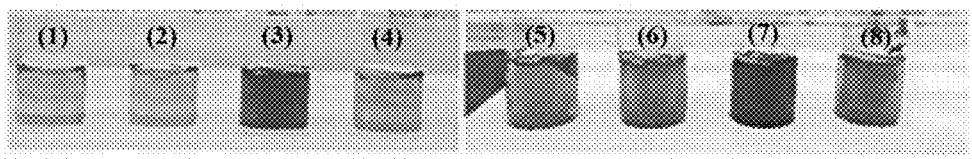
FIG. 2 is a photograph of vials containing solutions 1 to 8 as discussed in Reference Example 3.

A photograph of the test tube containing the solutions is shown in FIG. 2. Test tubes containing samples 1 to 8 as described in the table below are shown from left to right.

TABLE 5 appearance of the solutions investigated

| Sample | Oral care composition | pH | Colour |
|---|---|---|---|
| 1 | W | 7 | orange |
| 2 | X | 7 | orange |
| 3 | Y | 7 | blue |
| 4 | Z | 7 | orange |
| 5 | W | 9 | red |
| 6 | X | 9 | red |
| 7 | Y | 9 | blue-black |
| 8 | Z | 9 | red |

The data shown above illustrate that the same results were obtained at pH 7 and pH 9. Zincon may therefore be used to detect the release of zinc (II) from oral care compositions at pH 7.

Example 1

Determination of the Bioavailability of Zinc from Oral Care Compositions by Image Analysis A sheet of VITRO-SKIN was cut into equally-dimensioned pieces and hydrated in clarified saliva for 3-20 hours. After aspiration of the saliva, each piece was exposed to a toothpaste slurry consisting of 1 part by weight toothpaste to 2 parts by weight deionized water for a period of 10-15 minutes. A control piece was left untreated. The VITRO-SKIN was then removed from the slurries and rinsed with deionized water to remove any particulate matter.

An indicator solution consisting of 0.1% zincon and 0.2% xanthan gum, by weight, in 0.1 TRIS buffer. The pH of the indicator solution was pH 9. A 15 µL aliquot of the indicator solution was applied to each piece of VITRO-SKIN. The VITRO-SKIN pieces were lined up on a white paper and the indicator solution was applied before the VITRO-SKIN dried completely.

A digital camera was calibrated for white balance using a Munsell Color Control Standard in accordance with the manufacturer's instructions. The exposure bias of the digital camera was then increased by 1-2 units and the flash of the digital camera was turned off.

Digital photographs of the VITRO-SKIN pieces were taken 15 to 60 minutes after the application of the indicator solution and transferred to a computer. Images were opened in Adobe Photoshop and the image mode was changed from RGB to L-a-b. The portions of the image corresponding to the VITRO-SKIN pieces were selected and a color histogram generated. The intensity of the blue channel in the histogram was noted. Three repeat measurements were taken for each image.

The blue channel data are set out in Table 4.

TABLE 4 blue channel data for the oral care compositions investigated

| Oral care composition | Blue channel intensity/arbitrary units | | | Average | Average, blank subtracted | Standard deviation |
|---|---|---|---|---|---|---|
| | Reading 1 | Reading 2 | Reading 3 | | | |
| Blank | 164.22 | 165.23 | 165.35 | 164.93 | 0.00 | 0.62 |
| A | 146.41 | 146.89 | 147.58 | 146.96 | 17.97 | 0.59 |
| B | 133.54 | 133.89 | 133.68 | 133.70 | 31.23 | 0.18 |
| C | 99.73 | 99.80 | 99.58 | 99.70 | 65.23 | 0.11 |
| D | 98.68 | 98.43 | 98.35 | 98.49 | 66.45 | 0.17 |
| E | 118.58 | 118.62 | 118.31 | 118.50 | 46.43 | 0.17 |

Oral care compositions A to D are candidate oral care compositions. Oral care composition E is a commercially-available oral care composition. Each of oral care compositions A to E contains at least one zinc source. Based on the data shown in Table 4, the zincon assay ranks the oral care compositions in the following order based on their ability to deliver zinc (II): D≈C>E>B>A.

The ability of oral care compositions A to E to deliver zinc to tongue and buccal cells in vivo was assessed in a separate clinical trial.

For delivery to buccal cells, the clinical trial ranked the oral care compositions in the following order: D>C>>E>B>A. The blue channel data from the zincon assay were plotted against buccal cell zinc delivery data from the clinical trial. Linear regression gave a correlation coefficient ($R^2$) of 0.7461.

For delivery to tongue cells, the clinical trial ranked the oral care compositions in the order: C>D>E>B>A. The blue channel data from the zincon assay were plotted against tongue cell zinc delivery data from the clinical trial. Linear regression gave a correlation coefficient ($R^2$) of 0.7992.

In a comparative experiment, the uptake of zinc by vitro-skin from oral care compositions A to E was determined using atomic absorption spectroscopy (AAS). For tongue cells, the correlation coefficient ($R^2$) between the AES data and the clinical results was 0.672. For buccal cells, the correlation coefficient ($R^2$) was 0.8144.

Thus, it may be seen that the results obtained using zincon show good correlation with the results observed in clinical trials. Good correlation between the zincon measurements and those obtained using AES was also observed ($R^2$=0.9205). The zincon assay ranked the oral care compositions in the same order as the clinical trial conducted on delivery to buccal cells. Ti results of the zincon assay were also compatible with the results of the clinical trial for tongue cells.

In the present experiment, compositions C and D produced very similar results. Differences between these compositions were however resolved in the clinical trial. Both the zincon assay and the clinical trial indicated that compositions C and D deliver large amounts of zinc. The present inventors believe that the differences between compositions C and D could be resolved, more clearly by optimizing the zincon assay. In particular, it is believed that the use of a higher concentration of zincon would allow clearer differentiation between high-performing compositions.

Therefore, the present methods allow a straightforward assessment of zinc delivery which shows useful correlation with the results of clinical trials.

What is claimed is:

1. An in vitro method for determining the bioavailability of zinc (II) ions from an oral care composition comprising a zinc source, which method comprises:
   (i) providing a sample comprising the oral care composition;
   (ii) contacting the sample with a biorelevant substrate;
   (iii) separating the biorelevant substrate from the sample;
   (iv) contacting the biorelevant substrate with an indicator under conditions selected such that the indicator is capable of reacting with zinc (II) ions; and
   (v) determining a light absorbance of the indicator;
   wherein the indicator is zincon or a salt thereof.

2. The method of claim 1, wherein the biorelevant substrate is a soft tissue or a mimetic thereof.

3. The method of claim 2, wherein the biorelevant substrate is dermal tissue, a tissue from the oral cavity, or a mimetic thereof.

4. The method of claim 2, wherein the biorelevant substrate is a synthetic skin.

5. The method of claim 1, wherein the biorelevant substrate is a hard tissue or a mimetic thereof.

6. The method of claim 5, wherein the biorelevant substrate is a hydroxyapatite disc, a sea shell, or a mimetic thereof.

7. The method of claim 1, wherein the oral care composition is a toothpaste.

8. The method of claim 1, wherein the sample is a slurry comprising the toothpaste and a solvent.

9. The method of claim 8, wherein the ratio of the toothpaste to the solvent by weight is in the range 1:1 to 1:4.

10. The method of claim 1, wherein the sample includes natural or artificial saliva.

11. The method of claim 1, wherein the indicator is provided in an aqueous solution having a pH in the range of 7 to 9.5.

12. The method of claim 11, wherein the aqueous solution comprises a buffer selected from HEPES and TRIS.

13. The method of claim 11, wherein the aqueous solution has a pH in the range of 7 to 8.

14. The method of claim 11, wherein the aqueous solution includes a thickener.

15. The method of claim 1, wherein step (ii) comprises incubating the biorelevant substrate with the sample for a total duration in the range 10 to 20 minutes.

16. The method of claim 1, wherein step (v) comprises:
   (a) capturing a digital image of the biorelevant substrate; and
   (b) analysing the image in software.

* * * * *